(12) United States Patent
Fassbender et al.

(10) Patent No.: US 12,060,409 B2
(45) Date of Patent: Aug. 13, 2024

(54) SHORT CYCLIC PEPTIDES FOR THE TREATMENT OF GRAVES' DISEASE

(71) Applicant: ADVANCECOR GMBH, Martinsried (DE)

(72) Inventors: Julia Fassbender, Martinsried (DE); Hans-Peter Holthoff, Martinsried (DE); Zhongmin Li, Martinsried (DE); Martin Ungerer, Martinsried (DE)

(73) Assignee: ADVANCECOR GMBH, Martinsried (DE)

( * ) Notice: Subject to any disclaimer, the term of this patent is extended or adjusted under 35 U.S.C. 154(b) by 584 days.

(21) Appl. No.: 17/276,111

(22) PCT Filed: Sep. 13, 2019

(86) PCT No.: PCT/EP2019/074547
§ 371 (c)(1),
(2) Date: Mar. 12, 2021

(87) PCT Pub. No.: WO2020/053417
PCT Pub. Date: Mar. 19, 2020

(65) Prior Publication Data
US 2022/0041692 A1    Feb. 10, 2022

(30) Foreign Application Priority Data
Sep. 14, 2018 (EP) ..................... 18194531

(51) Int. Cl.
*C07K 14/00* (2006.01)
*C07K 14/72* (2006.01)
*A61K 38/00* (2006.01)

(52) U.S. Cl.
CPC ............ *C07K 14/723* (2013.01); *A61K 38/00* (2013.01)

(58) Field of Classification Search
CPC .............................. C07K 14/723; A61K 38/00
See application file for complete search history.

(56) References Cited

FOREIGN PATENT DOCUMENTS

EP           3 369 743 A1    9/2018
WO    WO 2015/019302 A2    2/2015

OTHER PUBLICATIONS

Hamidi et al. Endocrinology. 2013. 154(1): 562-571.*
Murakami M et al.: "Identification of immunogenic regions in human thyrotropin receptor for immunoglobulin G of patients with Graves' disease", Biochemical and Biophysical Research Communications, Elsevier, Amsterdam, NL, vol. 171, No. 1, Aug. 31, 1990, pp. 512-518, XP024771387, ISSN: 0006-291X, DOI: 10.1016/0006-291X(90)91423-P—Exhibit 3.
Sepehr Hamidi et al: "Probing Structural Variability at the N Terminus of the TSH Receptor with a Murine Monoclonal Antibody That Distinguishes between Two Receptor Conformational Forms", Endocrinology, vol. 154, No. 1, Jan. 1, 2013, pp. 562-571, XP055527649, US ISSN: 0013-7227, DOI: 10.1210/en.2012-1822—Exhibit 4.
De Grout L J; Shin Y Ha; Pan D; Gopalakrishnan G; Hennessey J V: "Evaluation of T cell stimulation by thyrotropin-receptor epitopes in Graves' disease", Journal of Endocrinological Investigation, vol. 32, No. 1, Jan. 1, 2009, pp. 52-56, XP009509715, ISSN: 0391-4097, DOI: 10.1007/U03345679—Exhibit 5.

* cited by examiner

*Primary Examiner* — Jeanette M Lieb
(74) *Attorney, Agent, or Firm* — ADRIANO & ASSOCIATES

(57) ABSTRACT

The present invention relates to short cyclic peptides, their use in the treatment, amelioration or prevention of a disease caused by antibodies targeting the thyrotropin-TSH receptor (TSHR) in the thyroid gland, in particular Graves' disease and orbitopathy, and to pharmaceutical compositions comprising the same.

12 Claims, 9 Drawing Sheets
Specification includes a Sequence Listing.

A

→ i.m. immunisations / ECG to measure heart rates
→ i.v. administration of peptides / vehicle (NaCl)
* blood withdrawals
° determination of T4 and/or anti-TSHR antibodies from serum samples
final ECG recordings / thyroid and orbital histopathology

B

SHORT CYCLIC PEPTIDES FOR THE TREATMENT OF GRAVES' DISEASE

This subject application claims priority under 35 U.S.C. § 371 to PCT Application No. PCT/EP2019/074547, filed Sep. 13, 2019, which claims the benefit of European Patent Application 18194531.2, filed Sep. 14, 2018. The contents of these applications are incorporated by reference in their entireties here.

FIELD OF THE INVENTION

The present invention relates to short cyclic peptides, their use in the treatment, amelioration or prevention of a disease caused by antibodies targeting the thyrotropin-TSH receptor (TSHR) in the thyroid gland, in particular Graves' disease and orbitopathy, and to pharmaceutical compositions comprising the same.

BACKGROUND OF THE INVENTION

Graves' disease is a common antibody-mediated autoimmune condition targeting the thyrotropin-TSH receptor (TSHR) in the thyroid gland, resulting in hyperthyroidism (1), with an annual incidence of 15-80 per 100,000 persons throughout the world. All existing treatment options are characterized by relatively high relapse rates, and significant side effect profiles (2). If left untreated, Graves' leads to significantly increased morbidity and mortality (3).

Treatments of refractory disease cases and of accompanying ophthalmopathy/orbitopathy are especially challenging. Ophthalmopathy occurs in almost half of all Graves' patients—up to 16 per 100,000 women per year in the general population (4). These patients must frequently be treated with high doses of intravenous corticoids over many weeks, which even incur more side effects (5). An alternative promise is offered by specific immune therapies which have been established for the treatment of allergic autoimmune conditions for more than 100 years (reviewed e.g. in 6, 7). In general, treatment with broad-range immunosuppressive drugs may cause serious side effects, so that such allergen-specific therapies are conceived to induce tolerance in a variety of related conditions. As a novel option, immunogen-mimicking cyclic peptides have been developed for the treatment of anti-TSHR antibody-mediated Graves' disease (8). A long-term disease model for human Graves' disease was successfully established with 9 immunizations of recombinant adenovirus expressing the extracellular A subunit of the TSHR (9,10) to permanently boost antibody production in mice. Monthly intravenous administration of cyclic peptides derived from the tertiary structure of TSHR subunit A resulted in strong potency to induce tolerance in TSHR-immunized diseased mice and a clear decrease of retro-orbital fibrosis (8).

EP 3369743 A1 discloses cyclic peptides suitable for the treatment, amelioration or prevention of a disease caused by antibodies targeting the thyrotropin-TSH receptor (TSHR) in the thyroid gland, in particular Graves' disease and orbitopathy. A length of the cyclic peptide equal or above 24 amino acids (primary structure) is taught to be necessary to obtain the reported effect. However, such long peptides of at least 24 amino acids are difficult and expensive to produce in suitable amounts.

SUMMARY OF THE INVENTION

In view of the above, it is the problem of the present invention to provide a further polypeptide which is suitable for the treatment, amelioration or prevention of a disease caused by antibodies targeting the thyrotropin-TSH receptor (TSHR) in the thyroid gland, in particular Graves' disease and orbitopathy, which do not show that above disadvantageous, in particular are easier and less expensive to produce in suitable amounts.

It has been surprisingly found that shortened cyclic peptides which were derived from the 1st or the 8th cylindrical loop of the leucine-rich repeat domain of TSHR also induced tolerance and successfully treated thyroid disease in animals, resulting in reduced thyroid size, normalized thyroid thyroxin (T4) levels, starting only 8 weeks after initiation of peptide therapy. It has also been founds that retro-orbital fibrosis was mitigated, suggesting a positive effect on Graves' orbitopathy. Tachycardia and cardiac hypertrophy were consistently reduced by the novel therapy.

The present invention provides cyclic peptides. Theses cyclic peptides may be used in the treatment or prevention of a disease caused by antibodies targeting the thyrotropin-TSH receptor (TSHR) in the thyroid gland, in particular Graves' disease and orbitopathy.

The present invention provides a cyclic peptide consisting of 9 to at most 15 amino acids and comprising an amino acid sequence of at least 9 amino acids which is present in one of the SEQ ID Nos. 1 or 8, or a derivative thereof, wherein one or two amino acids have been replaced by another amino acid or have been removed. Preferably, the peptide consists of 10 to at most 13 amino acids, more preferably of 11 or 13 amino acids.

As preferred embodiment, the cyclic peptide comprises the amino acid sequence
a) CHQEEDFRVTC, or a derivative thereof, wherein one or two amino acids have been replaced by another amino acid or have been removed, or
b) TKLDAVYLNKNKG, or a derivative thereof, wherein one to three amino acids have been replaced by another amino acid or have been removed.

As more preferred embodiment the peptide is of formula (I) or (II)

$$\text{cyclo}(x_{(i)}\text{CHQEEDFRVTC}z_{(j)}) \qquad (I),$$

$$\text{cyclo}(x_{(k)}\text{TKLDAVYLNKNKG}) \qquad (II),$$

wherein x and z are at each occurrence individually selected from an amino acid;
i is an integer from 0 to 4, j is an integer from 0 to 4, i+j≤4, and k is an integer of 0 to 2, and derivatives thereof, wherein one to three amino acids have been replaced by another amino acid or have been removed.

Further, the present invention provides a pharmaceutical composition comprising said cyclic peptides, and optionally a pharmaceutically acceptable carrier. The cyclic peptide and the pharmaceutical composition are used for the treatment, amelioration or prevention of a disease caused by antibodies targeting the thyrotropin-TSH receptor (TSHR) in the thyroid gland, in particular for the treatment, amelioration or prevention of Graves' disease, Graves' orbitopathy, Hashimoto's disease and/or hyperthyroidism as well as cardiovascular symptoms associated therewith.

BRIEF DESCRIPTION OF THE DRAWINGS

In the application and in the Figures, the peptides in accordance with the present invention are indicated as "P19" or "peptide19", and "P836 13mer", respectively.

DESCRIPTION OF THE PREFERRED EMBODIMENTS

Figure 1:
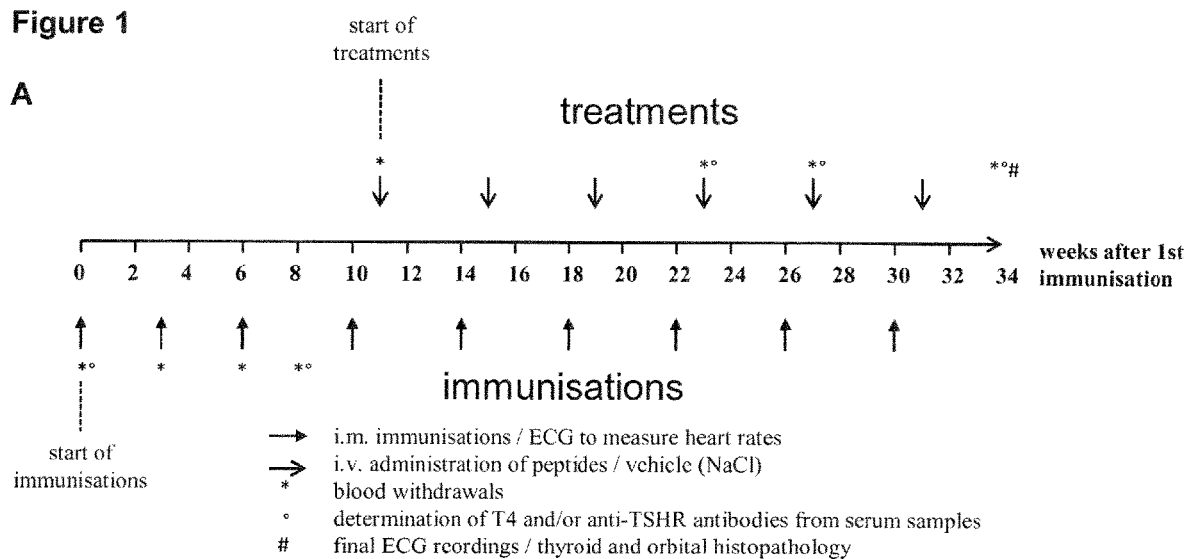
FIG. 1A shows a time schedule of the study comprising immunizations and therapy.
FIG. 1B shows a schematic structure of the thyroid stimulating hormone (TSH) receptor.
Figure 1:
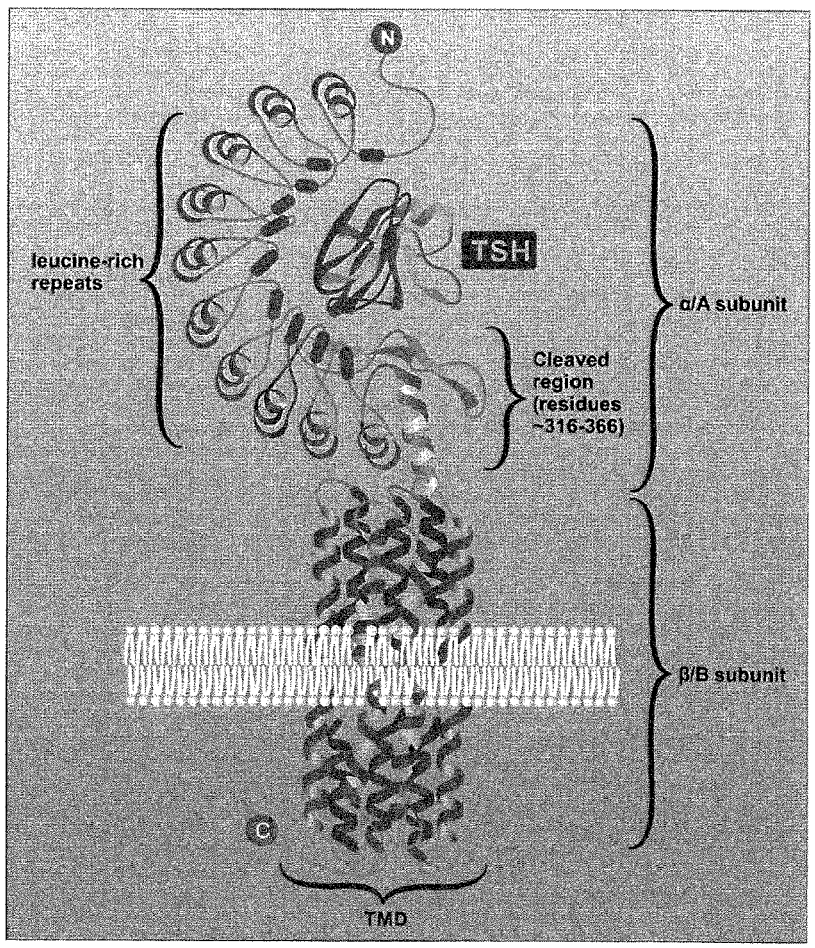

The present invention provides a cyclic peptide consisting of 9 to at most 15 amino acids and comprising an amino acid sequence of at least 9 amino acids which is present in one of the SEQ ID Nos. 1 or 8, or a derivative thereof, wherein one or two amino acids have been replaced by another amino acid or have been removed. Preferably, the peptide consists of 10 to at most 13 amino acids, more preferably of 11 or 13 amino acids. As preferred embodiment, the cyclic peptide comprises the amino acid sequence a) CHQEEDFRVTC, or b) TKLDAVYLNKNKG, or a derivative thereof, wherein one to three amino acids have been replaced by another amino acid or have been removed.

As more preferred embodiment the peptide is of formula (I) or (II)

$$\text{cyclo}(x_{(i)}\text{CHQEEDFRVTCz}_{(j)}) \quad (I),$$

$$\text{cyclo}(x_{(k)}\text{TKLDAVYLNKNKG}) \quad (II),$$

wherein x and z are at each occurrence individually selected from an amino acid;
i is an integer from 0 to 4, j is an integer from 0 to 4, i+j≤4, preferably i=j=0, and k is an integer of 0 to 2, preferably k=0, and derivatives thereof, wherein one or two amino acids have been replaced by another amino acid or have been removed.

The peptide is a cyclic peptide. Cyclic peptides can be obtained by cyclization of linear peptides, which are available by methods of peptide synthesis known in the art, e.g. solid phase peptide synthesis. The cyclization may occur by a linkage which is a covalent binding selected from the group comprising S—S linkages, peptide bonds, carbon bonds such as C—C or C═C, ester bonds, ether bonds, azo bonds, C—SC linkages, C—N—C linkages and C═N—C linkages. In one embodiment the S—S linkage is formed by two Cys residues of the peptide. The latter is preferred for the peptide of formula (I), wherein preferably i=0 and j=0. In case the cyclisation in the peptide of formula (I) is via an S—S linkage of the two Cys residues of the peptide, $x_{(i)}$ and $y_{(j)}$ represent side chains of the cyclic peptide linked via peptide bonds to the peptide backbone.

In another preferred embodiment the cyclization occurs by a peptide bond. The latter is preferred for the peptide of formula (II), wherein preferably k=0. Preferably, the peptide bond is formed by the NH2 group of the N-terminal amino acid and the COOH group of the C-terminal amino acid. Methods for such cyclization are well known in the art.

In an alternative embodiment additional bonds are formed by the side chain of NH2 groups and COOH groups of the constituent amino acids.

Without wishing to be bound by any theory in the following, the present inventors have surprisingly found that a number of short cyclic peptides are suitable for the treatment, amelioration or prevention of a disease caused by antibodies targeting the thyrotropin-TSH receptor (TSHR) in the thyroid gland, in particular for the treatment, amelioration or prevention of Graves' disease, Graves' orbitopathy and/or hyperthyroidism. In particular, it has been found that repeated 4-weekly intravenous administrations of 0.1 mg/kg bw cyclic peptide 19 which is a shortened derivate from the first cylindrical loop of the leucine-rich domain (LRD) of TSHR reduced thyroid hyperplasia in a long-term mouse model of Graves' disease. Also elevated thyroxin (T4) levels and sinus tachycardia were reduced, starting 8 weeks after initiation of peptide therapy. Administration of 0.3 mg/kg bw of the cyclic peptide 836 13mer (shortened derivate from the $8^{th}$ TSHR LRD) resulted in trends towards improvements of these parameters which did not reach statistical significance, but significantly improved retro-orbital fibrosis. Administration of the peptides in nave mice reconfirmed that the shorter cyclic peptides are not immunogenic on their own.

Compared to our previous study (8) these data show that markedly shortened TSHR epitope-derived cyclic peptides can be designed which still result in relevant therapeutic activity in the mouse Graves' disease model. The development leading to the present invention had been driven by the hypothesis that the 3-dimensional confirmation of the 10 TSHR LRD loops (13) should be sufficiently conserved by the design of cyclic peptides with potential activity, which ended up in 24-meric to 25-meric peptides (8). Since these peptides present a significant challenge for production and might also incur risks of immunogenicity upon long-term therapy, further development was necessary. It now has been found that it is actually feasible to reduce peptide length to 11- or 13-meric variants. Surprisingly, these shorter variants retain activity at smaller doses, so that intravenous peptide load could be reduced by ten-fold for two variants.

Peptide 19 is a shortened version of the 1st loop-derived cyclic peptide 829 which had been investigated in a previous study (8). It had been found that peptide 829 only resulted in small, non-significant trends to improve disease parameters. In contrast, peptide 19 whose sequence is derived from the same TSHR LRD area, but presents a 11-meric variant cyclized by a disulfide bond (not via the peptide backbone) was more effective than the 24-meric peptide 829. Therefore, the cyclic structure of the peptides (e.g. via C—C bonding) seems to be important, not just the amino acid sequence they derive from.

Serum samples from Ad-TSHR-immunized mice were used in an assay which determined binding of their sets of polyclonal anti-TSHR antibodies to TSHR-Fc ex vivo. Addition of cyclic peptide 19, but not of the cyclic peptide 836 13-mer ex vivo resulted in high affinity inhibition of these anti-TSHR antibody titers. In contrast, anti TSHR-antibody titers as determined in a slightly modified $3^{rd}$ generation assay using the monoclonal anti-TSHR antibody M22 were not affected by peptide therapy in vivo. Further it was investigated whether the peptides could inhibit the binding inhibition of M22 by human patient serum samples in a "3rd generation like" assay ex vivo, and also no significant effect of any of the investigated peptides was found. The failure to observe such an effect may also depend on the TSHR binding substrate in these "3$^{rd}$ generation like", M22-based assays, because this substrate has not been completely disclosed by the manufacturer and seems to derive from a porcine TSHR variant.

Also the effects of the novel peptides on the cardiac manifestations and complications of Graves' disease were investigated. Tachycardia is a reliable marker of disease severity in hyperthyroid patients (15,16). Regular ECG registrations served to detect the effect on heart rate. Treatment with peptide 19 significantly decreased the tachycardia which progressively developed in untreated TSHR-immunized mice over 3-9 months.

In summary, the present results show that treatment of clinical disease manifestations in a mouse model of Graves' disease by shortened TSHR LRD loop-mimicking cyclic peptides led to marked improvement of several disease parameters.

The cyclic peptide of the present invention consists of 9 to at most 15 amino acids and comprises a peptide of at least 9 amino acids which is present in one of the SEQ ID Nos. 1 or 8. The number of amino acids and thus the length of the primary structure appears to be crucial for the biological effects of the various peptides of the present invention. A length of the cyclic peptide from 9 to 15 amino acids (primary structure) is thought to be necessary and sufficient to obtain the reported results.

In accordance therewith, the invention relates to the general peptide structure as reflected by the above description. It will also be understood by the ones skilled in the art that the individual amino acid may be replaced by another naturally occurring or synthetic amino acid, preferably if both amino acids belong to the same category of amino acids. In accordance therewith, for example, an acidic amino acid can be replaced by another acidic amino acid, a basic amino acid may be replaced by another basic amino acid and so on. It will also be acknowledged by the ones skilled in the art that one or several of the amino acids forming the peptide of the present invention may be modified. In accordance therewith any amino acid as used herein preferably also represents its modified form. For example, an alanine residue as used herein also comprises modified alanine. Such modifications may, among others, be a methylation or acylation or the like, whereby such modification or modified amino acid is preferably comprised by the present invention as long as the thus modified amino acid and more particularly the peptide containing said thus modified amino acid is still functionally active as defined herein, more particularly functionally active in accordance with the present invention. Respective assays for determining whether such a peptide, i. e. a peptide comprising one or several modified amino acids, fulfils this requirement, are known to the one skilled in the art and, among others, also described herein, particularly in the examples.

The invention comprises also derivatives of the peptides such as salts with physiologic organic and inorganic acids like HCl, $H_2SO_4$, $H_3PO_4$, malic acid, fumaric acid, citric acid, tartaric acid, acetic acid, and trifluoroacetic acid.

According to the practice in the art, sequences of peptides are indicated from the N— terminus to the C— terminus, whereby the N— terminus is at the left side and the C— terminus is at the right side of the respective depicted amino acid sequence. The peptides as described herein are cyclic peptides, which do not have termini, as these are covalently linked.

In a preferred embodiment the amino acids, e.g. for x and z, are selected from acidic, basic, neutral and/or aliphatic amino acids. Preferably an acidic amino acid is an amino acid selected from the group comprising Asp, Asn, Glu, and Gln; preferably a basic amino acid is an amino acid selected from the group comprising Arg and Lys; preferably a neutral amino acid is an amino acid selected from the group comprising Gly, Ala, Ser, Thr, Val, Leu, He; preferably an aliphatic amino acid is an amino acid which is selected from the group comprising Gly, Ala, Ser, Thr, Val, Leu, He, Asp, Asn, Glu, Gln, Arg, Lys, Cys and Met.

As used herein, the expression that one particular amino acid, such as, e. g., a basic amino acid, is replaced by a different amino acid which is selected from a respective particular group of amino acids, such as, e. g., the group comprising basic amino acids, preferably means that the particular amino acid is replaced by another, i.e. different amino acid under the proviso that such different amino acid is part of the respective particular group of amino acids.

The cyclic peptides (also referred to herein as "active compound") of the invention can be incorporated into pharmaceutical compositions suitable for administration. Such compositions typically comprise the cyclic peptide and a pharmaceutically acceptable carrier. As used herein the language "pharmaceutically acceptable carrier" includes solvents, dispersion media, coatings, antibacterial and antifungal agents, isotonic and absorption delaying agents, which are compatible with pharmaceutical administration. Additional active compounds may be incorporated into the compositions.

A pharmaceutical composition of the invention is formulated to be compatible with its intended route of administration. Preferable routes of administration include parenteral, e.g., intravenous or intraarterial administration. Solutions or suspensions used for parenteral: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi.

The carrier can be a solvent or dispersion medium containing, for example, water, ethanol, polyol (for example, glycerol, propylene glycol, and liquid polyetheylene glycol), and mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

It is especially advantageous to formulate oral or parenteral compositions in dosage unit form for ease of administration and uniformity of dosage. Dosage unit form as used herein refers to physically discrete units suited as unitary dosages for the subject to be treated. Each unit contains a predetermined quantity of active compound calculated to produce the desired therapeutic effect in association with the required pharmaceutical carrier.

The active ingredient may be present in the pharmaceutical composition in the range of 1 µg/kg to 100 mg/kg, preferably 10 µg/kg to 1000 µg/kg, e.g. about 100 µg/kg, depending on the application form, preferably s.c. or i.v. application. A suitable dosing interval is from one week to three months, e.g. every two to four weeks.

It is within the present invention that the peptide and the pharmaceutical composition is used for the treatment of any of the diseases and patient groups as defined above including the treatment, amelioration or prevention of a disease caused by antibodies targeting the thyrotropin-TSH receptor (TSHR) in the thyroid gland in these patients by using the aforementioned compounds. Also, the peptides according to the present invention may be used for the preparation of a medicament for the treatment and/or prevention of any of the diseases and patient groups as defined above in connection with the pharmaceutical composition.

Finally, the present invention is related to a method for the treatment of patients as defined above, whereby the patient is in need of such treatment and whereby the method comprises administering to said patient a pharmaceutically effective amount of the peptide of the present invention, or the pharmaceutical composition or the medicament disclosed herein.

Preferably, a therapeutically effective dose refers to that amount of the active ingredient that produces amelioration of symptoms of a subject which can be determined by the one skilled in the art doing routine testing. A "patient" for the purposes of the present invention, i.e. to whom a compound according to the present invention or a pharmaceutical composition according to the present invention is administered, includes both humans and other animals and organisms. Thus the compounds, pharmaceutical compositions and methods are applicable to or in connection with both human therapy and veterinary applications, in the most preferred embodiment the patient is human.

LITERATURE

1. Weetman A P. Graves' disease. N Engl J Med 2000; 34:1236-1248.
2. Sundaresh V, Brito J P, Wang Z, Prokop L J, Stan M N, Murad M H, Bahn R S. Comparative effectiveness of therapies for Graves' hyperthyroidism: a systematic review and network meta analysis. J Clin Endocrinol Metab 2013; 98:3671-3677.
3. Abraham-Nordling M, Törring O, Hamberger B, Lundell G, Tallstedt L, Calissendorf J, Wallin G. Graves' disease: a long-term quality of life follow up of patients randomized to treatment with antithyroid drugs, radioiodine or surgery. Thyroid 2005; 15:1279-1285.
4. Bahn R S. Graves' ophthalmopathy N Engl J Med 2010; 362:726-738.
5. Stan M N, Garrity J A, Carranza Leon B G, Prabin T, Bradley E A, Bahn R S. Randomized Controlled Trial of Rituximab in Patients With Graves' Orbitopathy. J Clin Endocrinol Metabol 2015; 100:432-441.
6. Larche M, Wraith D C. Peptide-based therapeutic vaccines for allergic and autoimmune diseases. Nature Med 2005; 11(4):S69-S76.
7. Soyka M, van de Veen W, Holzmann D, Akdis M, Akdis C A. Scientific foundations of allergen-specific immunotherapy for allergic diseases. Chest 2014; 146:1347-1357.
8. Holthoff H P, Li Z, Fassbender J, Reimann A, Adler K, Münch G, Ungerer M. Cyclic peptides for effective treatment in a long-term model of Graves' disease and orbitopathy. Endocrinology 2017; 158 (7): 2376-2390.
9. Holthoff H P, Göbel S, Li Z M, Fassbender J, Reimann A, Zeibig S, Lohse M J, Münch G, Ungerer M. Prolonged TSH receptor A subunit immunization of female mice leads to a long-term model of Graves' disease, tachycardia and cardiac hypertrophy. Endocrinology 2015; 156: 1577-1589.
10. Ungerer M, Fassbender J, Li Z, Münch G, Holthoff H P. Review of mouse models of Graves' disease and orbitopathy novel treatment by induction of tolerance. Clin Rev Allerg Immunol 2017; 52(2):182-193.
11. Parmentier M, Libert F, Maenhaut C, Lefort Gerard C, Peret J, Van Sande J, Dumont J E, Vassart G. Molecular cloning of the thyrotropin receptor. Science 1989; 246: 1620-1622.
12. Nagayama Y, Kaufman K D, Seto P, Rapoport B. Molecular cloning, sequence and functional expression of the cDNA for the human thyrotropin receptor: Biochem Biophys Res Commun 1989; 165: 1184-1190.
13. Nunez MigUel R, Sanders J, Chirgadze D Y, Furmaniak J, Rees Smith B. Thyroid stimulation autoantibody M22 mimics TSH binding to the TSH receptor leucine rich domain: a comparative structural study of protein-protein interactions. J Mol Endocrin 2009; 42:381-395.
14. Neumann S, Place R F, Krieger C C, Gershengorn M C. Future prospects for the treatment of Graves' hyperthyroidism and eye disease. Horm Metab Res 2015; 47:789-796.
15. Klein I, Ojamaa K. Thyroid hormone and the cardiovascular system. New Engl J Med 2001; 344:501-509.
16. von Olshausen K, Bischoff S, Kahaly G, Mohr-Kahaly S, Erbel R, Beyer J, Meyer J. Cardiac arrhythmias and heart rate in hyperthyroidism. Am J Cardiol 1989; 63: 930-933.
17. Blank M, Shoenfeld Y. B cell targeted therapy in autoimmunity. J Autoimmunity 2007; 28:62-68.

The present invention will now be further illustrated by the following figures and examples.

FIG. 1A shows the time course of immunizations, administrations of therapeutic peptides and measurements. At 0 weeks immunisations started, at 11 weeks treatments started.

"-▶" (filled arrow) indicates i.m. immunisations/ECG to measure heart rates; "→" (open arrow) indicates i.v. administrations of peptides/vehicle (NaCl); * indicates blood withdrawals; ° indicates determination of T4 and/or anti-TSHR antibodies from serum samples; #indicates final ECG recordings/Thyroid and orbital histopathology.

FIG. 1B shows a schematic structure of the thyroid stimulating hormone (TSH) receptor. The cyclic peptides in accordance with the invention were derived from the eighth loop structure of the leucine-rich repeat domain of the extracellular A subunit of the TSHR, as marked in darker colour.

Figure 2:
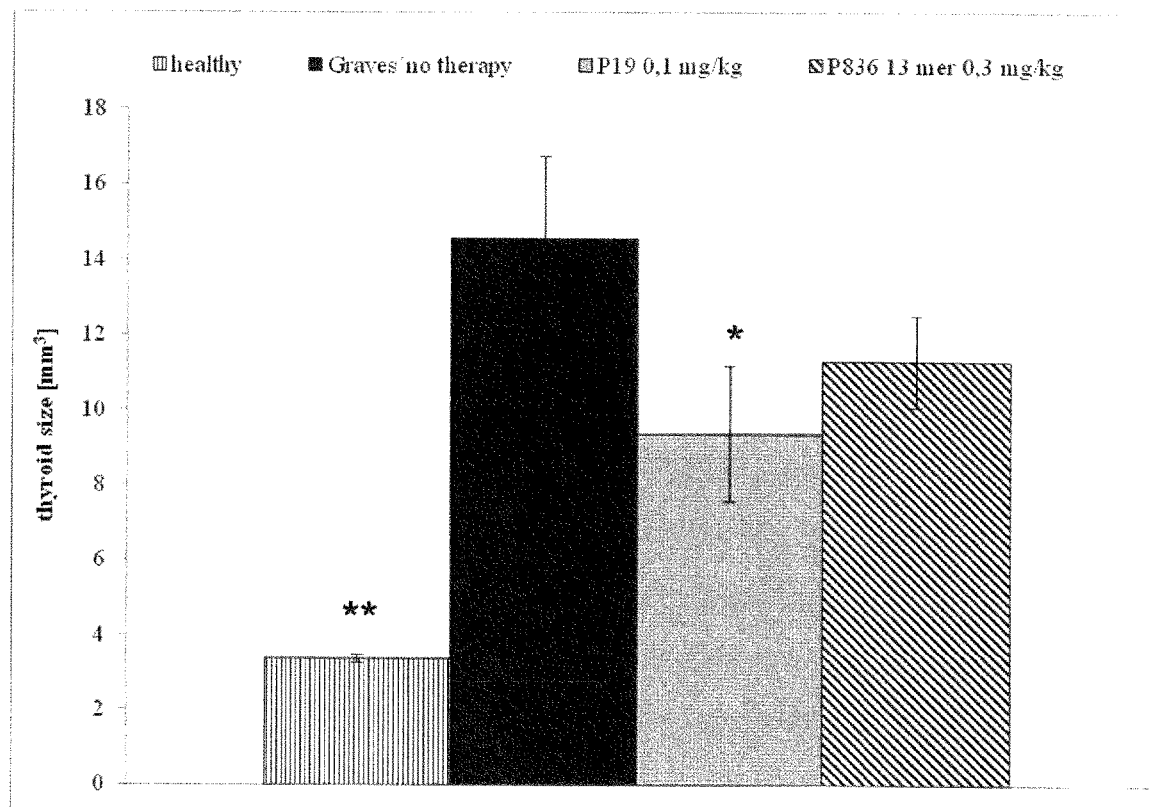
FIG. 2 shows the effect of the peptide of the present invention on thyroid size.

FIG. 2 shows the effect of peptide therapy on macroscopically measured thyroid size. Thyroid sizes were investigated at the end of the experiment. The measurements were carried out in Ad-TSHR-immunized mice treated by either 4-weekly injections with vehicle (0.9% NaCl, "Graves' no therapy", n=10 mice), or administrations of 0.3 mg/kg body weight of peptide 836 13mer (11 mice), or 0.1 mg/kg body weight of peptide 19 ("P19", 10 mice). In addition, age-matched immunologically naïve unimmunized mice ("healthy", 10 animals) were investigated. The mean thyroid sizes in $mm^3$ are shown with SEM.

Differences between groups were tested by AVOVA followed by post hoc LSD testing. * $p<0.05$, ** $p<0.001$ compared to the TSHR-immunized group treated with only NaCl ("Graves' no therapy").

Figure 3:
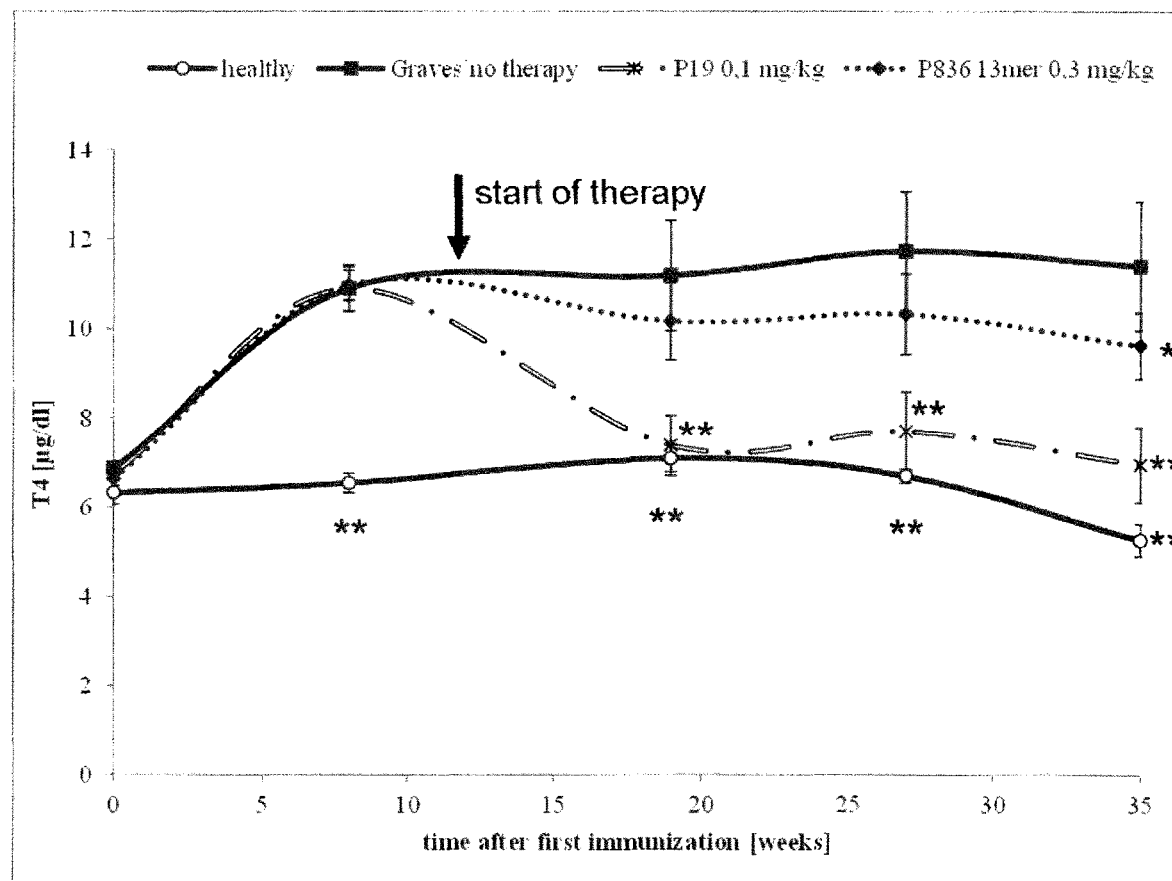
FIG. 3 shows the effect of the peptides of the present invention on serum thyroxin (T4) levels.

FIG. 3 shows the effects of peptide therapy on serum thyroxin (T4) levels. The measurements were carried out in Ad-TSHR-immunized mice treated by either 4-weekly injections with vehicle (0.9% NaCl, "Graves' no therapy", n=10 mice), or administrations of 0.3 mg/kg body weight of peptide 836 13mer (11 mice), or 0.1 mg/kg body weight of peptide 19 ("P19", 10 mice). In addition, age-matched immunologically naïve unimmunized mice ("healthy", 10 animals) were investigated. Data are represented as means±SEM. Significance over time was tested by analysis of variance (ANOVA) of groups at given time points, and controlled by ANOVA for repeated measurements within one group, followed by LSD post-hoc testing. *$p<0.05$, and **$p<0.01$, compared to the TSHR-immunized group treated with only NaCl ("Graves' no therapy").

Figure 4:
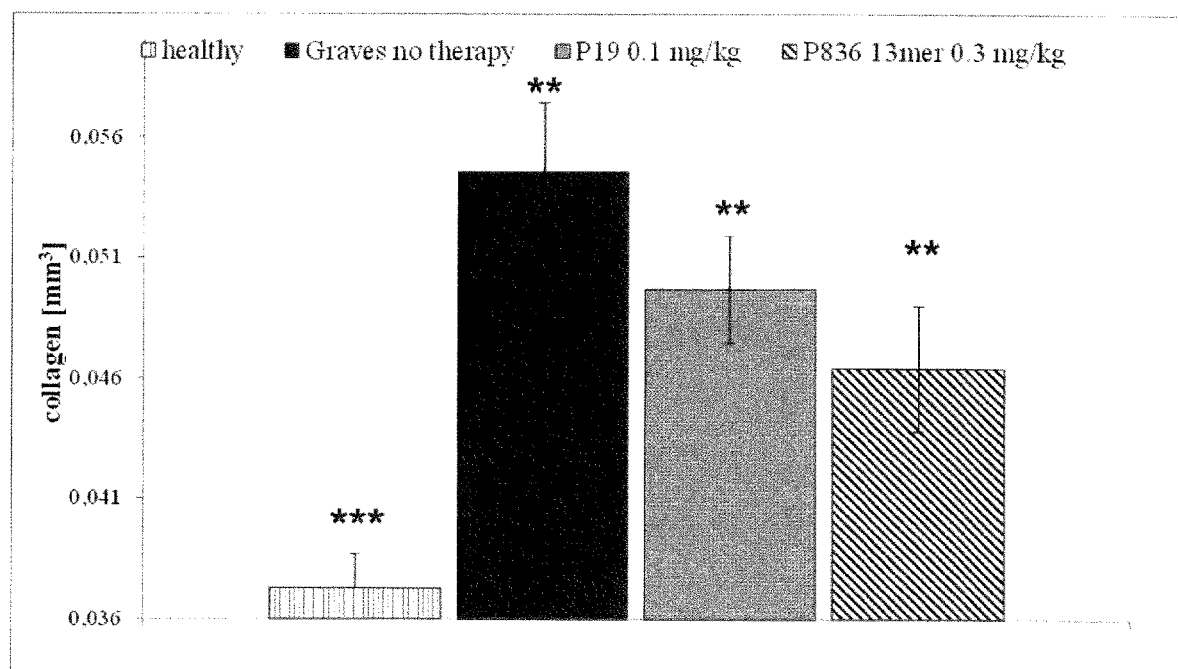
FIG. 4 shows the effect of the peptides of the present invention on digitized analysis of retroorbital fibrosis volumes after histological preparation of orbital sections.

FIG. 4 shows the effect of peptide therapy on digitized analysis of retroorbital fibrosis volumes ($mm^3$ collagen) after histological preparation of orbital sections. The effects of peptide therapy on severity of retro-orbital fibrosis were evaluated in histological sections of all available animals. The measurements were carried out in Ad-TSHR-immunized mice treated by either 4-weekly injections with vehicle (0.9% NaCl, "Graves' no therapy", n=10 mice), or administrations of 0.3 mg/kg body weight of peptide 836 13mer (11 mice), or 0.1 mg/kg body weight of peptide 19 ("P19", 10 mice). In addition, age-matched immunologically naïve unimmunized mice ("healthy", 10 animals) were investigated. The mean total fibrosis volumes of each all orbitae (left and right), as assessed by digitized image analysis of all sections, and consecutive integrations, are shown with SEM. Differences between groups were tested by ANOVA, *$p<0.01$, '$p<0.001$ compared to the TSHR-immunized group treated with only NaCl ("Graves' no therapy").

Figure 5:
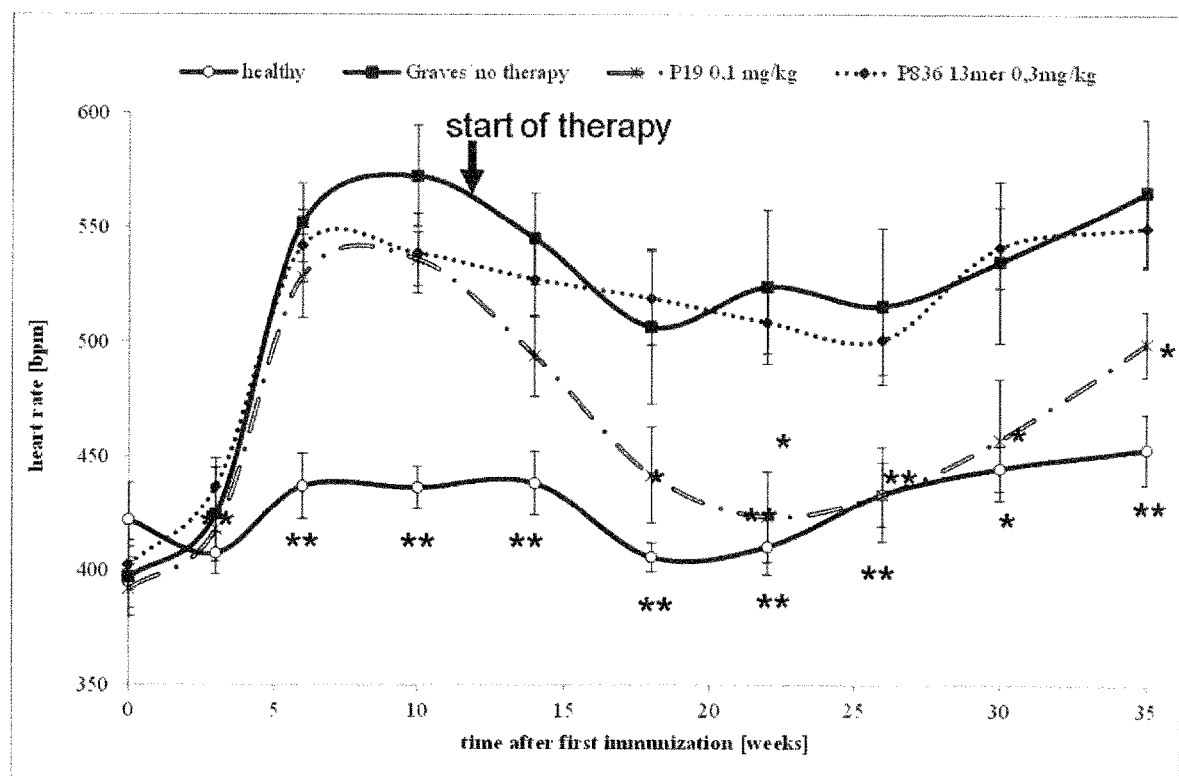
FIG. 5 shows the effect of the peptides of the present invention on heart rate.

FIG. 5 shows the effects of peptide therapy on heart rates at various times. The heart rates were evaluated in all animals. The measurements were carried out in Ad-TSHR-immunized mice treated by either 4-weekly injections with vehicle (0.9% NaCl, "Graves' no therapy", n=10 mice), or administrations of 0.3 mg/kg body weight of peptide 836 13mer (11 mice), or 0.1 mg/kg body weight of 19 ("P19", 10 mice). In addition, age-matched immunologically naïve unimmunized mice ("healthy", 10 animals) were investigated. Data are represented as mean±SEM. Significance over time was tested by analysis of variance (ANOVA) of groups at given time points, and controlled by ANOVA for repeated measurements within one group, followed by LSD post-hoc testing.*$p<0.05$, and **$p<0.005$, compared to the TSHR-immunized group treated with only NaCl ("Graves' no therapy").

Figure 6:
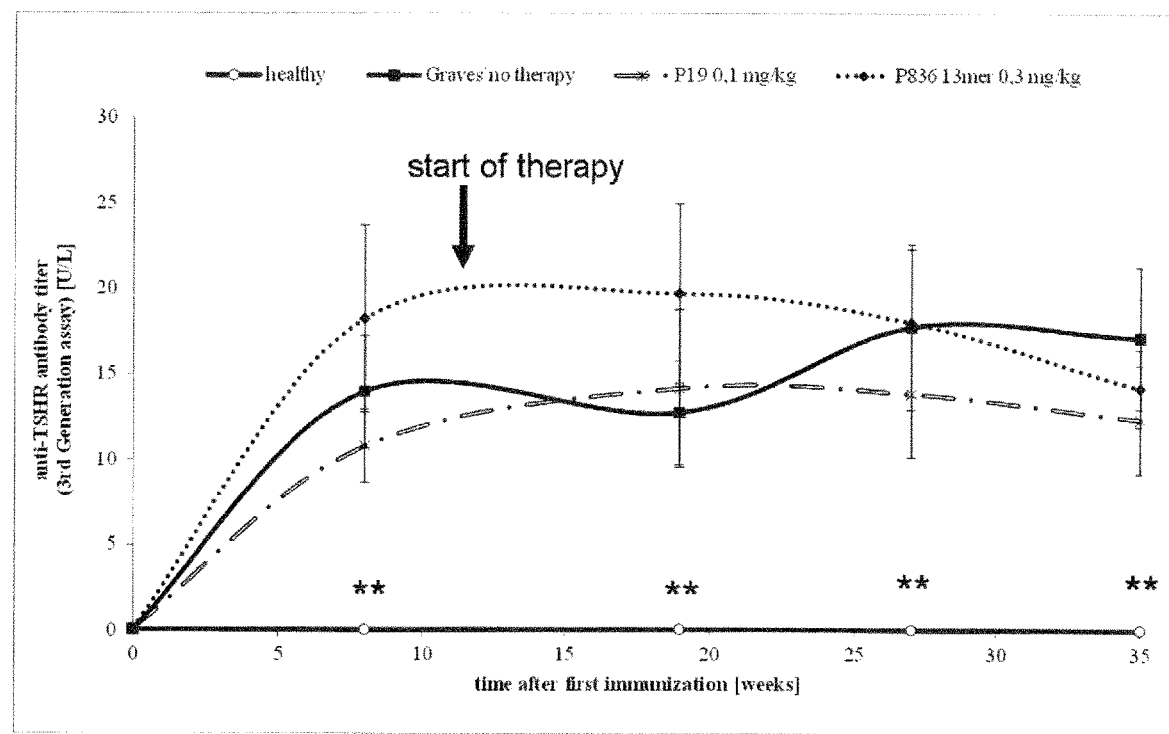
FIG. 6 shows the effect of the peptides of the present invention on time course of anti-TSHR titers.

FIG. 6 shows the effect of peptide on time course of anti-TSHR titers, as measured by $3^{rd}$ generation ELISA, in which serum samples are used to determine inhibition of M22-binding to coated plates. The measurements were carried out in Ad-TSHR-immunized mice treated by either 4-weekly injections with vehicle (0.9% NaCl, "Graves' no therapy", n=10 mice), or administrations of 0.3 mg/kg body weight of peptide 836 13mer (11 mice), or 0.1 mg/kg body weight of peptide 19 ("P19", 10 mice). In addition, age-matched immunologically naïve unimmunized mice ("healthy", 10 animals) were investigated. Data are represented as mean±SEM. Significance over time was tested by analysis of variance (ANOVA) of groups at given time points, and controlled by ANOVA for repeated measurements within one group, followed by LSD post-hoc testing. **$p<0.001$, compared to the TSHR-immunized group treated with only NaCl ("Graves' no therapy")

Figure 7:
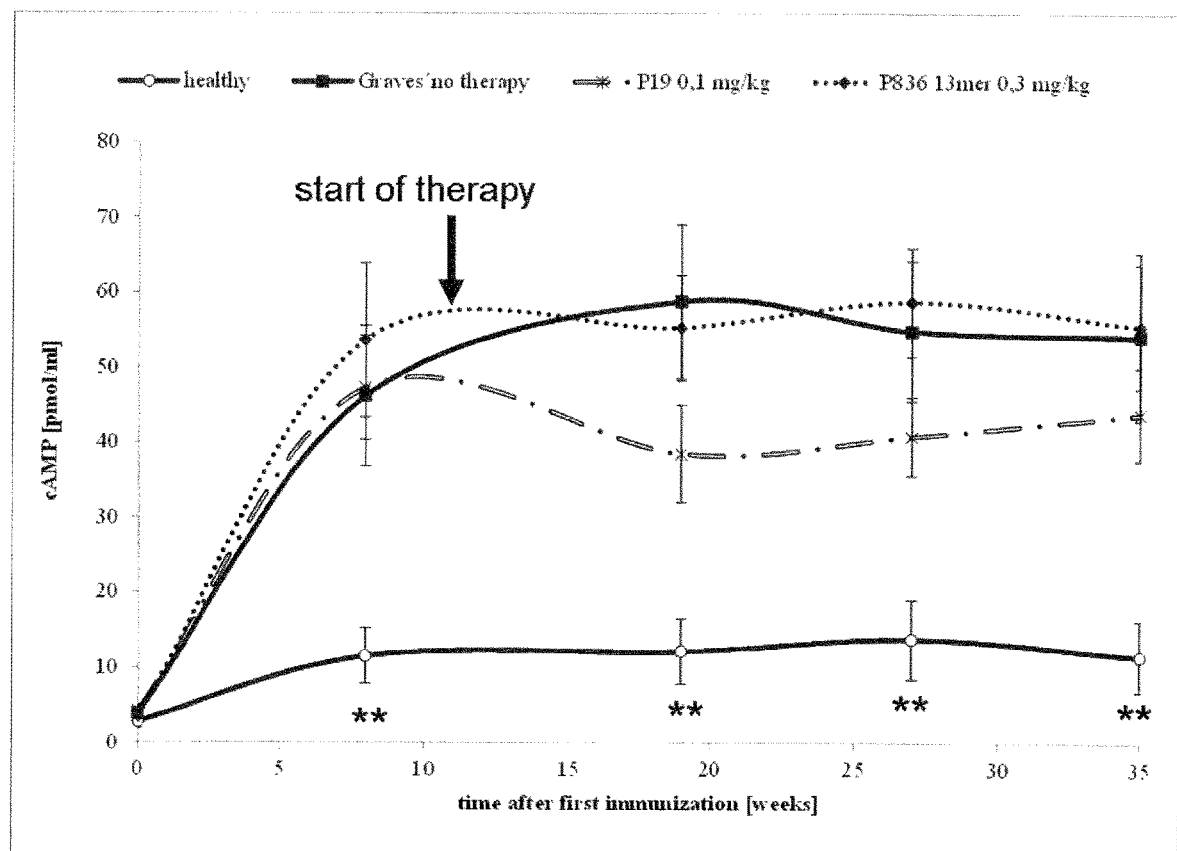
FIG. 7 shows the effect of the peptides of the present invention on cAMP stimulation in TSHR-expressing test cells.

FIG. 7 shows the effect of peptide therapy on cAMP stimulation in TSHR-expressing test cells, as determined in sera taken from the mice during the experiment. The effects of peptide therapy on the capacity of anti-TSHR antibodies to stimulate cAMP generation were evaluated in CHO cells expressing the human TSHR. The measurements were carried out in Ad-TSHR-immunized mice treated by either 4-weekly injections with vehicle (0.9% NaCl, "Graves' no therapy", n=10 mice), or administrations of 0.3 mg/kg body weight of peptide 836 13mer (11 mice), or 0.1 mg/kg body weight of peptide 19 (10 mice). In addition, age-matched immunologically naïve unimmunized mice ("healthy", 10 animals) were investigated. Data are represented as mean±SEM. Differences between groups were tested by AVOVA followed by post hoc LSD testing. **$p<0.01$ compared to the TSHR-immunized group treated with only NaCl ("Graves' no therapy")

Figure 8:
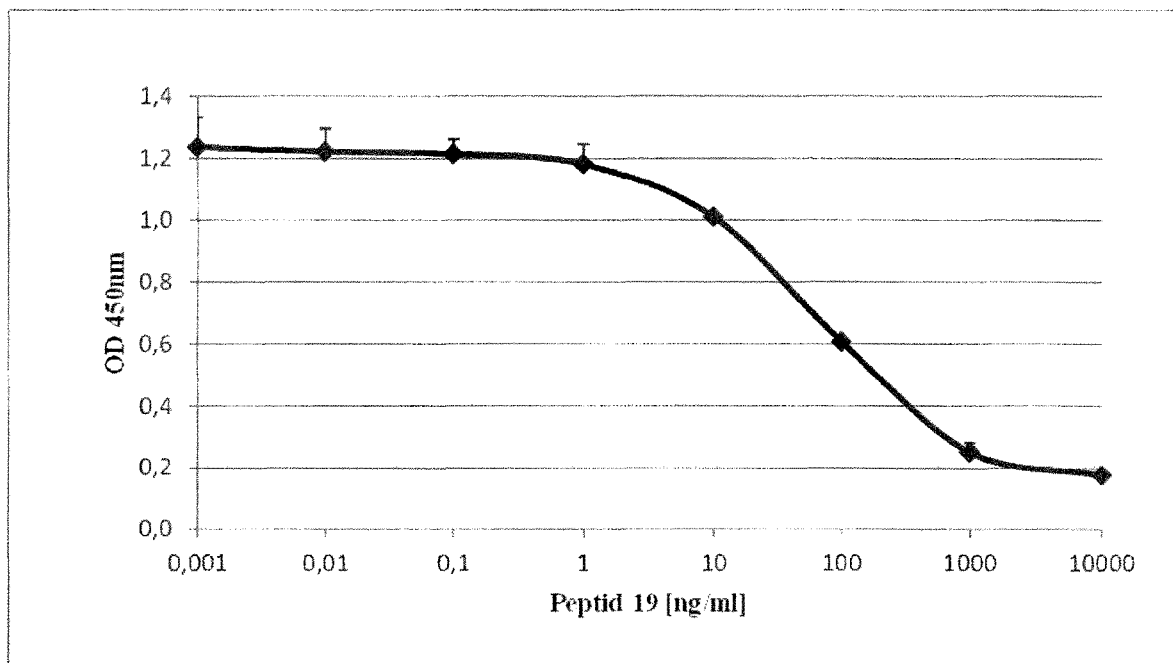
FIG. 8 shows the effect of peptide 19 of the present invention on anti-TSHR antibody titers in Ad-TSHR-immunized mouse serum samples.

FIG. 8 shows the effect of peptide 19 of the invention on anti-TSHR antibody titers from Ad-TSHR-immunized mice ex vivo. Each measurement was carried out in 4 samples. Results are shown as optical density (OD) 450 values with standard errors of the means (SEM).

Figure 9:
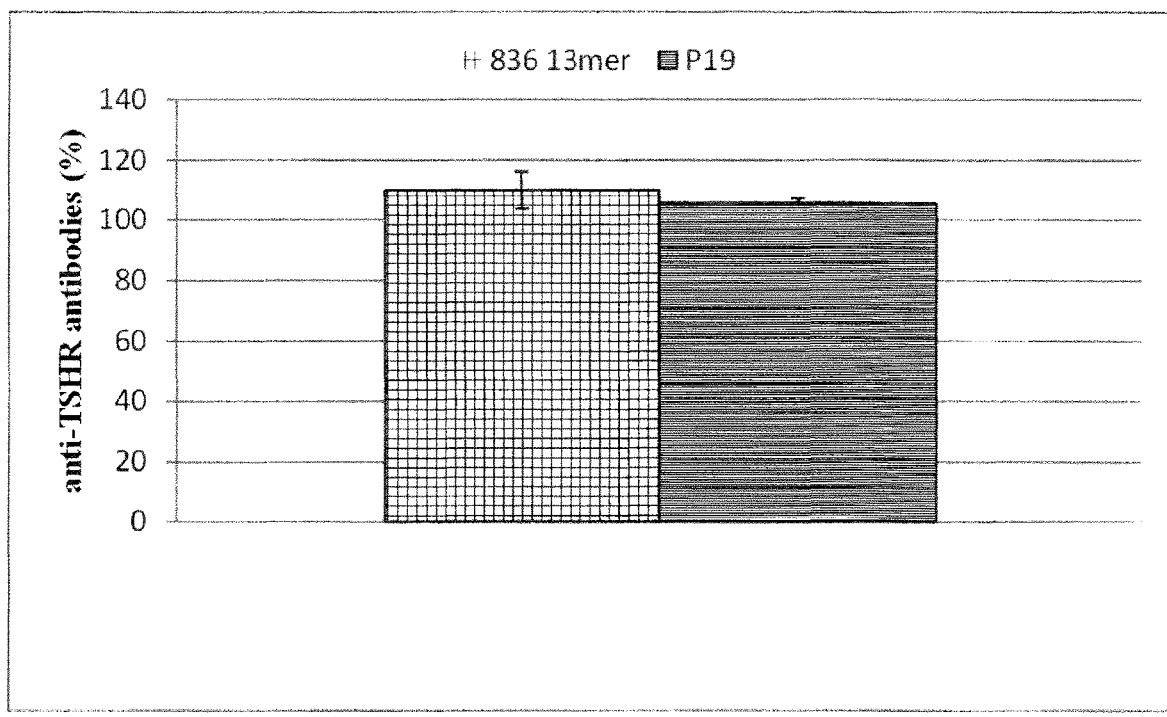
FIG. 9 shows the effect of the peptides of the present invention ex vivo on anti-TSHR antibody titers, as determined in a double approach in a modified $3^{rd}$ generation assay.

FIG. 9 shows the effect of the peptides of the invention ex vivo on anti-TSHR antibody titers, as determined in a double approach in a modified $3^{rd}$ generation assay (detected by competing with the monoclonal anti-TSHR antibody M22). Each measurement was carried out in 4 samples. Results are shown as % of untreated controls with standard errors of the means (SEM). Significance was tested by analysis of variance (ANOVA) between groups, followed by LSD post-hoc testing. There were no statistically relevant differences between groups. **$p<0.01$ versus TSHR-immunized, no therapy.

EXAMPLES

Materials and Methods
Recombinant Adenovirus

The DNA sequence coding for the first 289 amino acids of the human TSH-receptor (11, 12) was cloned into the Microbix Admax™ adenovirus expression system as described before (9). HEK293A cells were used to propagate until first viral plaques became visible. This system results in recombinant replication-deficient E1 and E3-deficient adenovirus type 5. A control adenovirus containing only the reporter gene GFP (Ad-GFP) was amplified and purified in the same manner.

Synthesis of Cyclic Peptides

The cyclic peptides of the invention are derived from peptides with structural homology to the first and eighth of the 10 cylindrical loops of the TSHR leucine rich domain as outlined in Table 1.

TABLE 1

TSHR-Peptide sequences of the regions of the cylindrical loops of the TSHR leucine rich domain

| Peptide # | (derived from TSHR sequence aa): | | |
|---|---|---|---|
| 829 | 26-49 | SPPCECHQEEDFRVTCKDIQRIPS | (SEQ ID No. 1) |
| 830 | 50-73 | LPPSTQTLKLIETHLRTIPSHAFS | (SEQ ID No. 2) |
| 831 | 73-89 | SNLPNISRIYVSIDVTL | (SEQ ID No. 3) |
| 832 | 98-121 | YNLSKVTHIEIRNTRNLTYIDPDA | (SEQ ID No. 4) |
| 833 | 122-145 | LKELPLLKFLGIFNTGLKMFPDLT | (SEQ ID No. 5) |
| 834 | 146-163 | KVYSTDIFFILEITDNP | (SEQ ID No. 6) |
| 835 | 170-193 | NAFQGLCNETLTLKLYNNGFTSVQ | (SEQ ID No. 7) |
| 836 | 194-217 | GYAFNGTKLDAVYLNKNKYLTVID | (SEQ ID No. 8) |
| 837 | 218-237 | KDAFGGVYSGPSLLDVSQTS | (SEQ ID No. 9) |
| 838 | 242-265: | PSKGLEHLKELIARNTWTLKKLPL | (SEQ ID No. 10) |

Specifically, the 13-meric peptide 836, also termed herein "P836 13mer" (a peptide of the present invention) replicates a peptide of the eighth cylindrical loop. "Peptide 19" or "P19" (a peptide of the present invention) is a shorted version of peptide 829 which was designed in analogy to the first loop of the TSHR LRR.

The proteins were synthesized by Biosyntan Berlin according to described protocols of fluorenylmethoxycarbonyl (FMOC) resin-based amino acid chain elongation, and subsequent head-to-tail cyclisation. Fmoc amino acid or Fmoc dipeptide was attached to the 2-Chlorotrityl chloride resin (RAPP Polymere GmbH, Germany) yielding a loading of 0.30 mmol/g resin. Peptide synthesis was done by a standard cycle of deblocking with 30% piperidine/N,N-dimethylformamide (DMF, 5+12 min) and coupling with 3 eq. Fmoc-amino acid/0-(7-Azabenzotriazol-1-yl)-N,N,N',NI-tetramethyluronium-hexafluorphosphate (HATU)/6 eq. N-methylmorpholine (NMM) in DMF (double coupling, 2×30 min). After cleavage from the resin by 20% hexafluoroisopropanol (HFIP)/DCM (2×20 min) the isolated crude peptide was cyclized by 1.5 eq 7-Azabenzotriazol-1-yloxy) tripyrrolidinophosphonium hexafluorophosphate (PyAOP)/3 eq diisopropylethylamine (DIEA) in DMF over night, the solvent evaporated and the crude peptide deblocked by trifluoroacetic acid (TFA)/water/thioanisol (TIS) (95:5:3) during 2 h. Then, the peptides were purified up to 95% by means of HPLC and analyzed by MALDI-TOF mass spectrometry. This quality control reconfirmed that amino acids had been correctly included into the peptides, and their cyclisation was evident from the experimental determination versus theoretical prediction of molecular weights: As examples, values of observed versus predicted molecular weight were 1446.2 vs. 1445.7 for peptide 13-mer 836, and 1364.6 vs. 1363.5 for peptide 19.

Studies in Immunized Mice

Female BALB/c mice were delivered from Charles River, Sulzfeld, Germany, and were adapted for at least one week to start experiments at the age of 6 weeks. Animals were kept under standard housing conditions (23±2° C., 55±10% RH) in groups of ten animals in GR1800DD cages (Tecniplast®).

All animal experiments were approved by the local animal welfare authority and Ethics committee at the Regierung von Oberbayern (Government of Upper Bavaria) in Munich, Germany (no. 55.2-1-54-2531-25-12), and carried out in accordance to the World Medical Association (Declaration of Helsinki), and the European Commission guidelines (Directive 2010/63/EU). All guidelines for care of animals were respected.

Mice received $10^{10}$ plaque-forming units (pfu) of adenovirus carrying the A-subunit of the TSHR gene. In addition, age-matched immunologically naïve mice (10 animals) were studied for comparison. For immunisation, mice were anaesthetized with isoflurane (introduction 5%, maintenance 1.5-2%) and placed on a heating pad. The adenovirus was injected into the left and right femoral muscles in a volume of 25 µl each.

For blood withdrawal, mice were moved to a restrainer. 100 µl of blood was withdrawn out of the left or right tail vein with a 27G needle. Blood was centrifuged at 2400 g for 15 minutes at room temperature and serum was stored at −20° C. At the end of the study (before euthanasia), blood was withdrawn intracardially in deep anesthesia (170 mg/kg ketamine+17 mg/kg xylazine) with a 1 ml syringe and a 24G needle and treated as mentioned above.

The study protocol used three 3-weekly immunizations ("initiation"), followed by a "maintenance" phase with further regular 4-weekly boosts until the 9$^{th}$ immunisation, as described before (9). Strict inclusion and exclusion criteria were defined before starting the study: If T4 thyroxin values in Ad-TSHR-immunized mice were at least 25% higher at week 11 compared to basal measurement at week 0, mice were included for further study. Consequently, 25% of immunized mice were excluded before randomization because they did not meet this threshold. Also, mean T4 values and basal heart rates of all groups had to be consistently altered. Mice were randomly assigned to therapeutic groups, allocations were concealed, and veterinarians and all other staff who handled the animals, or who analysed the results were strictly blinded to the treatment groups. Therapy (either peptides or 0.9% NaCl vehicle control) was given 1 week after the 4th immunization by IV injection into a tail vein, and then continued at 4-weekly intervals, as described before (8). A detailed immunisation schedule is shown in FIG. 1A. All animals which were excluded after randomisation are reported in results. When mice were subjected to anaesthesia for immunisation, their heart function was monitored with an electrocardiogram (ECG amplifier module, Harvard Apparatus, Hugo Sachs electronics) and recorded with a special software, which allows to determine the heart rate from the ECG reading (Haemodyn, Hugo Sachs electronics). ECG was also performed in anaesthesia before animals were euthanized for histological exam at the end of the study. Total thyroxine (T4) was measured by immunoassay kit (#T4044T-100, Calbiotech Inc, Austin, CA) in duplicate determination.

Histological Analysis

After euthanasia, dissection of the thyroid glands was performed under a stereomicroscope, as described before (8). The orbital sections were viewed at 4× objective lens (Axioscope, Zeiss), captured with an Axiovision digital cam system and recorded with 2560×1920 pixel resolution. Focus was adjusted for each new field, but light conditions were kept identical. All sections were evaluated in a blinded fashion.

Fibrosis areas in the extra-orbital adipose tissue and extra-orbital muscle (EOM) regions were indicated by their green colour. Digitized image analysis of green colour pixels was carried out using the luminescence tool of Adobe Photoshop software version CS5 extended on the basis of pixel areas. In order to correct for possible bias between stainings, the green staining intensity of the respective orbital bone in each section was taken as an internal standard for each measurement. Accordingly, all fibrotic tissue throughout a whole orbital section was quantified, and results of all sections were added in the end to yield a total fibrosis volume (mm$^3$) of each investigated orbita (taking account of the 0.63 mm interval thicknesses between sections).

Measurements in Mouse Sera

Anti-TSHR autoantibody titers and potency of antibodies to stimulate TSHR-dependent cAMP levels in test cells were determined before start of immunisation (basal value), 56 days after first immunisation, 133 days after first immunisation, and 189 days after first immunisation, and at the end of experiment. To this aim, 2 different assays were used:

1) "3$^{rd}$ generation assay": Antibodies against TSHR were detected by a commercially available 3$^{rd}$ generation enzyme immunoassay provided by RSR Limited, Avenue Park, Pentwyn, Cardiff, U.K., in which the of the human Graves patient-derived M22 monoclonal antibody and serum antibodies compete for binding sites on immobilized TSHR. The assay is also used in Roche's Cobas® assay (04388790) for ECLIA with minor modifications. The assay was performed using 30 1 1:10 (PBS) diluted serum in at least double determination according to the manufacturer's instructions.

2) Thyroid stimulating antibodies in the serum of hyperthyroid mice were analysed by measuring cyclic adenosine monophosphate (cAMP) generation in Chinese hamster ovary (CHO) cells JP2626 expressing the human TSHR (kindly provided by Dr. Gilbert Vassart, Brussels, Belgium). CHO cells were seeded into 96-well plates (30000 cells per well) and incubated for 24 hours in Dulbecco's modified Eagle medium (DMEM, Invitrogen Ltd) containing 2% fetal calf serum. Then, DMEM was removed and mice serum was diluted 1:8 in 40 μl HBSS buffer (20 mM Hepes, 1.26 mM $CaCl_2$), 5.33 mM KCl, 0.44 mM $KH_2PO_4$, 0.5 mM $MgCl_2$, 0.4 mM $MgSO_4$, 4.2 mM $NaHCO_3$, 5.6 mM glucose, and 222 mM Sucrose, pH7.2) supplemented with 1.5% BSA and 0.5 mM isobutyl-1-methylxanthine (Sigma-Aldrich, Pole, UK) and added to each well. After incubation for 2.5 hours at 37° C. the cAMP release in the medium was measured in duplicates by a competitive immunoassay ELISA (#EMSCAMPL, Thermo Fisher Scientific, Waltham, MA, USA).

In Vitro Studies

In order to investigate the direct binding of peptides to anti-TSHR antibodies in vitro, ELISA plates were coated with 0.5 μg/ml TSHR-Fc in coating solution for 1 h. All subsequent procedures were performed at room temperature (RT) and incubations were on a microtiter plate shaker. The coated plates were washed three times with PBST, blocked with 100 μl/well of blocking solution, (PBS with 0.1% Tween, 3% milk powder) for 1 h, and washed again. The blocked ELISA plates were then incubated for 1 h with polyclonal mouse anti-TSHR antibodies pre-incubated (30 min) with different concentrations of peptide 19 diluted in PBST. After washing with PBST, the ELISA plates were incubated with 100 μl/well of anti-mouse IgG detection antibody, labelled with POD, for 1 h. After washing, the POD was detected by incubation with 100 μl/well of TMB substrate until a maximal optical density (OD) of about 1 to 2 was reached. Finally, the colorimetric reaction was stopped with 100 μl/well stopping solution and the OD determined at a wavelength of 450 nm with a reference wave length of 595 nm with the Tecan Infinite F 200 plate reader.

The peptides were also investigated in 3$^{rd}$ generation assays with minor modifications: 30 μl of the diluted monoclonal M22-Bio antibody was mixed with 30 μl diluted peptide (final concentration of 100 μg/ml in PBS) and added to the TSHR-pre-coated microtiter plate. After an incubation step for 2 h at room temperature the protocol was continued according to the manufacturer's instructions.

Studies in Native Mice

BALB/c mice were adapted for at least one week to start experiments at the age of 12 weeks. Animals were kept as described before. This study was approved by the local animal welfare authority and Ethics committee at the Regierung von Oberbayern (Government of Upper Bavaria) in Munich, Germany (no. 55.2-1-54-2532.0-32-15), and carried out in accordance to the European Commission guidelines.

Peptides (1 mg/kg body weight) or NaCl vehicle control were given by IV injection into a tail vein of these naïve mice (n=6 per group), and then continued at 4-weekly intervals for 6 months, as described before for the therapeutic study in immunized mice. Serum samples were taken at identical intervals.

Statistics

Differences between the groups were analysed by ANOVA for comparison between groups using SPSS software (version 19), followed by LSD (least significant difference) post-hoc testing, or Student's t test where appropriate. For comparison of values at various times within one group, ANOVA for repeated measurements (RM-ANOVA) was used where appropriate.

Results

Selection of Cyclic Peptides

Cyclic peptides were synthetised whose amino acid sequences and tertiary structures were derived from the TSHR leucin-rich domain (LRD)—(cf. Table 1 shown above).

Short peptide 836 is a 13-meric cyclic peptide having the sequence TKLDAVYLNKNKG (SEQ ID No.11), which is based on the eighth TSHR LRD loop, and peptide 19 (11-meric) having the sequence CHQEEDFRVTC (SEQ ID No.12), which is based on the first loop of the TSHR LRD.

In several pilot studies, optimal dosing of these peptides was evaluated by studying their effects on major outcome parameters. Hence, it was determined that 0.3 mg/kg body weight peptide 836 13-mer yielded best results, as well as 0.1 mg/kg peptide 19. Therefore, these doses were chosen to carry out a randomized, blinded main study these results are shown in the following. No animals were prematurely taken out of the study after randomization, and the prespecified protocol was completed in all animals. Results reflect the respective means of all values of all randomized animals.

Thyroid Sizes, as Determined from Serial Sections

Thyroid volumes (mm$^3$) were determined from the sum of the areas of each section over the whole cutting region (between 5 and 10 slides, depending on respective size of the thyroid gland) multiplied by the slice thickness of 0.5 mm. This macroscopic investigation showed clearly increased thyroid sizes in mice which had received 9 immunisations of Ad-TSHR (see FIG. 2), compared to the healthy mouse group. In contrast, peptide 19-treated animals showed significantly decreased thyroid sizes, whereas treatments with 836 13-mer resulted in trends towards reduced sizes which did not reach statistical significance.

Determination of Thyroxin Serum Levels

Thyroxin (T4) levels did not differ between groups at study start, and mean T4 levels in eligible animals of the Ad-TSHR-immunized groups were significantly higher than controls at week 11 (start of therapy, FIG. 3). After start of therapy, peptide 19-treated animals showed progressively decreasing T4 levels. These values even reverted to normal values in the peptide 19-treated group. In contrast, peptide 836 13 mer-treated mice showed a trend which did not reach statistical significance.

Patho-Histological Changes of the Orbits

Histological investigation of retro-orbital fibrosis was carried out after serial sectioning of the orbitae. In 9×AdTSHR-treated mice, a significant increase of retro-orbital fibrosis was observed upon digitized image analysis which was markedly reduced in 836 13mer-treated mice, whereas a trend was observed in the peptide 19-treated group which did not reach statistical significance (FIG. 4).

ECG to Determine Heart Rates

Starting from the 3$^{rd}$ immunisation, a significant increase in heart rate in the hyperthyroid Ad-TSHR immunized group was observed (FIG. 5). In contrast, heart rate in the native, healthy group was only mildly increased at older age, but did not change significantly.

Upon consecutive Ad-TSHR-immunizations, a further strong increase in heart rate in the hyperthyroid vehicle-treated group was observed. In contrast, peptide 19-treated animals showed some larger variation, but significantly decreased resting heart rates at later time points. In contrast, peptide 836 13mer-treated mice showed trends towards reduced heart rates which did not reach statistical significance.

Anti-TSHR Antibody Titers and Capacity to Stimulate cAMP in Test Cells

Anti-TSHR antibodies were determined from serum samples by investigating the ability of the respective mouse sera to inhibit the binding of the monoclonal Graves' patient antibody M22 to the TSHR ("3$^{rd}$ generation ELISA"). Highly significant titers were detected in all Ad-TSHR-immunized animals (FIG. 6). As in previous studies, there were no statistically significant variations of anti-TSHR titers in vivo between groups.

In addition, the stimulatory activity of these antibodies was determined as the capacity of mouse serum samples to induce an increase in TSHR-dependent cAMP levels in test cells (FIG. 7). Anti-TSHR antibodies from almost all TSHR-immunized mice showed potency to stimulate cAMP in TSHR-expressing test cells. The maximum inducible cAMP levels showed considerable variation. Peptide therapy did not impact on these mean TSHR-dependent cAMP formations.

In Vitro Studies: ELISA

To characterize the effects of the cyclic peptides ex vivo/in vitro, we carried out 2 ELISA assays. In contrast to the observed lacking inhibitory effects of all peptides in the canonical 3$^{rd}$ generation assay in vivo (FIG. 6), we found a clear inhibition of peptide 19 on an in vitro assay: When added to sera from Ad-TSHR-immunized mice, peptide 19 inhibited the binding of the polyclonal anti-TSHR antibodies, which were contained therein, to coated TSHR-Fc effectively at a low IC50 value of about 20 nmol/L (FIG. 8). However, these ex vivo effects were not observed for peptide 836 13-mer.

Further it was investigated whether the peptides could inhibit the binding inhibition of M22 by human patient serum samples in a "3rd generation like" assay ex vivo. Results are shown in FIG. 9: There was no difference in anti-TSHR antibody titers between peptide groups (final concentration: 100 µg/mL) versus controls.

Studies in Immunologically Naive Mice

All immunologically naïve mice tolerated 6 monthly administrations of either 1 mg/kg bw cyclic peptide 836 13mer, peptide 19 or vehicle (NaCl) equally well—no pathological clinical findings were observed. Generation of anti-TSHR antibodies was not observed in any of the peptide-treated animals over 6 months—all measured titers were below background, so that no immune response to either peptide was documented. No statistically significant difference occurred between peptide-treated and vehicle-treated groups (as assessed by either t-test or ANOVA).

The invention claimed is:

1. A cyclic peptide consisting of 9 to at most 15 amino acids and comprising an amino acid sequence of at least 9 amino acids which is present in one of the SEQ ID Nos. 1 or 8, or a salt thereof.

2. The cyclic peptide according to claim 1, which peptide consists of 10 to at most 13 amino acids.

3. The cyclic peptide according to claim 1, which peptide consists of 11 or 13 amino acids.

4. The cyclic peptide according to claim 1, wherein the peptide comprises a) SEQ ID NO 11: CHOEERDERVTC, or a salt thereof, or b) SEQ ID NO 12: TKLDAVYLNKNKG, or a salt thereof.

5. The cyclic peptide according to claim 4, wherein the peptide is of formula (I) or (II)

$$\text{cyclo}(x_{(i)}\text{CHQEEDFRVTC}z_{(j)}) \quad (I),$$

$$\text{cyclo}(x_{(k)}\text{TKLDAVYLNKNKG}) \quad (II),$$

wherein
x and z are at each occurrence individually selected from an amino acid;
i is an integer from 0 to 4, j is an integer from 0 to 4, 1+j≤4, and k is an integer of 0 to 2,
and salts thereof.

6. The cyclic peptide according to claim 5, wherein i=0 and j=0, or k=0.

7. A pharmaceutical composition comprising the cyclic peptide according to claim 1, and optionally a pharmaceutically acceptable carrier.

8. A method for the treatment, amelioration or prevention of a disease caused by antibodies targeting the thyrotropin-TSH receptor (TSHR) in the thyroid gland of a subject by administering an acceptable amount of a cyclic peptide according to claim 1 to the subject thereby treating, ameliorating or preventing the disease in the subject.

9. A method for the treatment, amelioration or prevention of Graves' disease, Graves' orbitopathy and/or hyperthyroidism in a subject by administering an acceptable amount of a cyclic peptide according to claim 1 to the subject thereby treating, ameliorating or preventing Graves' disease, Graves' orbitopathy and/or hyperthyroidism in the subject.

10. A method for the treatment, amelioration or prevention of a disease caused by antibodies targeting the thyrotropin-TSH receptor (TSHR) in the thyroid gland by administering an acceptable amount of pharmaceutical composition of claim 7 to the subject thereby treating, ameliorating or preventing the disease in the subject.

11. A method for the treatment, amelioration or prevention of Graves' disease, Graves' orbitopathy and/or hyperthyroidism by administering an acceptable amount of pharmaceutical composition of claim 7 to the subject thereby treating, ameliorating or preventing Graves' disease, Graves' orbitopathy and/or hyperthyroidism in the subject.

12. The cyclic peptide according to claim 1, wherein the peptide binds thyroid-stimulating anti-TSHR antibodies.

* * * * *

SEQUENCE LISTING

<160> NUMBER OF SEQ ID NOS: 12

<210> SEQ ID NO 1
<211> LENGTH: 24
<212> TYPE: PRT
<213> ORGANISM: artificial
<220> FEATURE:
<223> OTHER INFORMATION: Amino acid sequence derived from human
      thyrotropin-TSH receptor (TSHR)

<400> SEQUENCE: 1

Ser Pro Pro Cys Glu Cys His Gln Glu Glu Asp Phe Arg Val Thr Cys
1               5                   10                  15

Lys Asp Ile Gln Arg Ile Pro Ser
            20

<210> SEQ ID NO 2
<211> LENGTH: 24
<212> TYPE: PRT
<213> ORGANISM: artificial
<220> FEATURE:
<223> OTHER INFORMATION: Amino acid sequence derived from human
      thyrotropin-TSH receptor (TSHR)

<400> SEQUENCE: 2

Leu Pro Pro Ser Thr Gln Thr Leu Lys Leu Ile Glu Thr His Leu Arg
1               5                   10                  15

Thr Ile Pro Ser His Ala Phe Ser
            20

<210> SEQ ID NO 3
<211> LENGTH: 17
<212> TYPE: PRT
<213> ORGANISM: artificial
<220> FEATURE:
<223> OTHER INFORMATION: Amino acid sequence derived from human
      thyrotropin-TSH receptor (TSHR)

<400> SEQUENCE: 3

Ser Asn Leu Pro Asn Ile Ser Arg Ile Tyr Val Ser Ile Asp Val Thr
1               5                   10                  15

Leu

<210> SEQ ID NO 4
<211> LENGTH: 24
<212> TYPE: PRT
<213> ORGANISM: artificial
<220> FEATURE:
<223> OTHER INFORMATION: Amin acid sequence derived from human
      thyrotropin-TSH receptor (TSHR)

<400> SEQUENCE: 4

Tyr Asn Leu Ser Lys Val Thr His Ile Glu Ile Arg Asn Thr Arg Asn
1               5                   10                  15

Leu Thr Tyr Ile Asp Pro Asp Ala
            20

<210> SEQ ID NO 5
<211> LENGTH: 24
<212> TYPE: PRT
<213> ORGANISM: artificial
<220> FEATURE:
<223> OTHER INFORMATION: Amin acid sequence derived from human
      thyrotropin-TSH receptor (TSHR)

<400> SEQUENCE: 5

Leu Lys Glu Leu Pro Leu Leu Lys Phe Leu Gly Ile Phe Asn Thr Gly
1               5                   10                  15

Leu Lys Met Phe Pro Asp Leu Thr
            20

<210> SEQ ID NO 6
<211> LENGTH: 17
<212> TYPE: PRT
<213> ORGANISM: artificial
<220> FEATURE:
<223> OTHER INFORMATION: Amin acid sequence derived from human
      thyrotropin-TSH receptor (TSHR)

<400> SEQUENCE: 6

Lys Val Tyr Ser Thr Asp Ile Phe Phe Ile Leu Glu Ile Thr Asp Asn
1               5                   10                  15

Pro

<210> SEQ ID NO 7
<211> LENGTH: 24
<212> TYPE: PRT
<213> ORGANISM: artificial
<220> FEATURE:
<223> OTHER INFORMATION: Amin acid sequence derived from human
      thyrotropin-TSH receptor (TSHR)

<400> SEQUENCE: 7

Asn Ala Phe Gln Gly Leu Cys Asn Glu Thr Leu Thr Leu Lys Leu Tyr
1               5                   10                  15

Asn Asn Gly Phe Thr Ser Val Gln
            20

<210> SEQ ID NO 8
<211> LENGTH: 24
<212> TYPE: PRT
<213> ORGANISM: artificial
<220> FEATURE:
<223> OTHER INFORMATION: Amin acid sequence derived from human
      thyrotropin-TSH receptor (TSHR)

<400> SEQUENCE: 8

Gly Tyr Ala Phe Asn Gly Thr Lys Leu Asp Ala Val Tyr Leu Asn Lys
1               5                   10                  15

Asn Lys Tyr Leu Thr Val Ile Asp
            20

<210> SEQ ID NO 9
<211> LENGTH: 20
<212> TYPE: PRT
<213> ORGANISM: artificial
<220> FEATURE:
<223> OTHER INFORMATION: Amin acid sequence derived from human
      thyrotropin-TSH receptor (TSHR)

<400> SEQUENCE: 9

Lys Asp Ala Phe Gly Gly Val Tyr Ser Gly Pro Ser Leu Leu Asp Val
1               5                   10                  15

Ser Gln Thr Ser
            20

<210> SEQ ID NO 10
<211> LENGTH: 24
<212> TYPE: PRT
<213> ORGANISM: artificial

```
<220> FEATURE:
<223> OTHER INFORMATION: Amin acid sequence derived from human
      thyrotropin-TSH receptor (TSHR)

<400> SEQUENCE: 10

Pro Ser Lys Gly Leu Glu His Leu Lys Glu Leu Ile Ala Arg Asn Thr
1               5                   10                  15

Trp Thr Leu Lys Lys Leu Pro Leu
            20

<210> SEQ ID NO 11
<211> LENGTH: 13
<212> TYPE: PRT
<213> ORGANISM: artificial
<220> FEATURE:
<223> OTHER INFORMATION: Amino acid sequence derived from human
      thyrotropin-TSH receptor (TSHR)

<400> SEQUENCE: 11

Thr Lys Leu Asp Ala Val Tyr Leu Asn Lys Asn Lys Gly
1               5                   10

<210> SEQ ID NO 12
<211> LENGTH: 11
<212> TYPE: PRT
<213> ORGANISM: artificial
<220> FEATURE:
<223> OTHER INFORMATION: Amino acid sequence derived from human
      thyrotropin-TSH receptor (TSHR)

<400> SEQUENCE: 12

Cys His Gln Glu Glu Asp Phe Arg Val Thr Cys
1               5                   10
```